Figure 1:
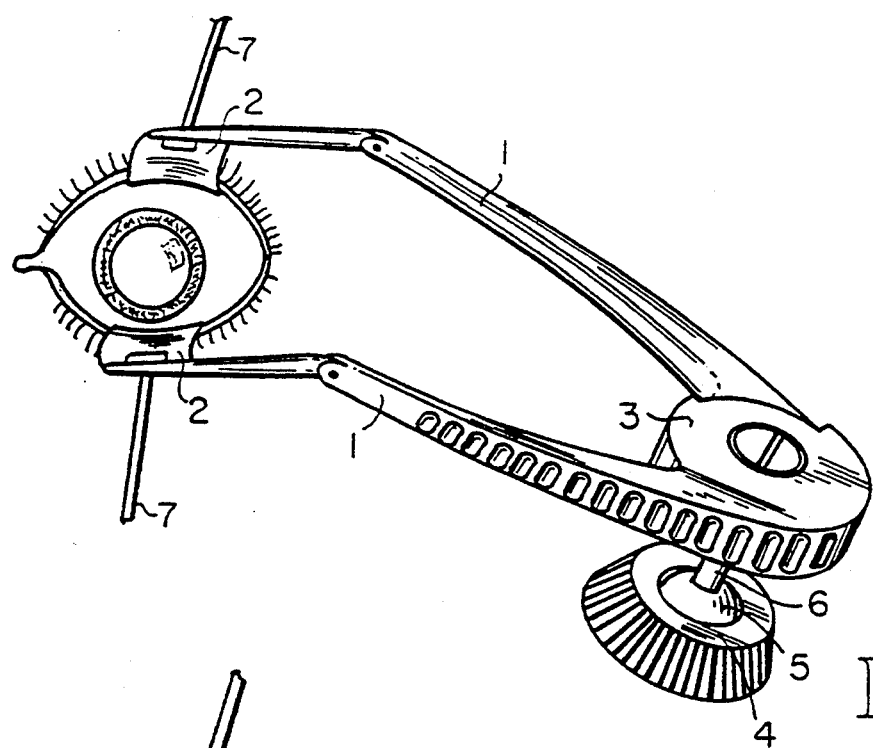

United States Patent [19]

Grounauer

[11] Patent Number: 5,341,798

[45] Date of Patent: * Aug. 30, 1994

[54] RETRACTOR DEVICE FOR HUMAN OR ANIMAL TISSUE

[76] Inventor: Pierre-Alain Grounauer, Rue de l'Ale 38, CH-1003 Lausanne, Switzerland

[*] Notice: The portion of the term of this patent subsequent to Dec. 10, 2008 has been disclaimed.

[21] Appl. No.: 985,359

[22] Filed: Dec. 2, 1992

Related U.S. Application Data

[63] Continuation of Ser. No. 794,565, Nov. 19, 1991, abandoned, which is a continuation-in-part of Ser. No. 397,446, Jul. 21, 1989, Pat. No. 5,070,860.

[30] Foreign Application Priority Data

Dec. 4, 1987 [CH] Switzerland ............... 4735/87-0

[51] Int. Cl.⁵ .............................................. A61B 17/02
[52] U.S. Cl. .................................................... 128/20
[58] Field of Search ............................. 138/17, 18, 20

[56] References Cited

U.S. PATENT DOCUMENTS

| | | |
|---|---|---|
| 1,706,500 | 3/1929 | Smith . |
| 2,642,862 | 6/1953 | Jackson ............. 128/20 |
| 2,702,590 | 2/1955 | Debeh ............... 128/20 |
| 3,490,455 | 1/1970 | Illig ................... 128/20 |
| 3,651,689 | 3/1972 | Haddad .............. 128/17 |
| 4,037,589 | 7/1977 | McReynolds ....... 128/20 |
| 4,321,916 | 3/1982 | McKee . |
| 4,412,532 | 11/1983 | Anthony ............ 128/20 |
| 4,621,619 | 11/1986 | Sharpe ............... 128/20 |

FOREIGN PATENT DOCUMENTS

| | | |
|---|---|---|
| 156218 | 10/1985 | European Pat. Off. . |
| 2951664A1 | 2/1981 | Fed. Rep. of Germany . |
| 3535045A1 | 4/1987 | Fed. Rep. of Germany . |

OTHER PUBLICATIONS

Niesel, "Eye Surgery", 1980 pp. 73–78.

*Primary Examiner*—Mark S. Graham
*Attorney, Agent, or Firm*—Woodard, Emhardt, Naughton, Moriarty & McNett

[57] ABSTRACT

The retractor device for human or animal tissues, and more particularly for retracting upper and lower eyelids to expose the underlying eyeball for surgery, comprises a pair of retracting arms each having a spoon articulatingly mounted at one first end of said retracting arm to pivot about an axe that is in substantially perpendicular relationship with said retracting arm. A retracting means joins the second ends of the arms in a cooperating relationship and biases the first ends of said retracting arms into retracted positions. Each spoon has a first curvature adapted to the shape of an eyeball and a second curvature adapted to the shape of an eyelid.

4 Claims, 3 Drawing Sheets

RETRACTOR DEVICE FOR HUMAN OR ANIMAL TISSUE

This application is a continuation of application Ser. No. 07/794,565, filed Nov. 19, 1991, now abandoned, which application was a continuation-in-part application of Ser. No. 07/397,446, filed Jul. 21, 1989, now U.S. Pat. No. 5,070,860.

The mechanical devices for the retraction of human or animal tissues have to make it possible to see the subjacent anatomic elements, thereby making visible an operative area. These devices for making accessible previously concealed tissues are particularly useful in connection with microsurgical operations, particularly of the eye or for the functional exploration of the latter. They enable the edges of a cutaneous incision to be kept spaced apart, without any force other than that provided by the said device.

Known at the present time are numerous devices which have for their purpose to retract the eyelids and to hold them spaced from the eyeball. In particular, one example of such a device is described in U.S. Pat. No. 4,037,589. This device is very rudimentary and comprises only a metallic loop, the concave ends of which permit the retraction of the eyelids. Another example of known device is described in U.S. Pat. No. 1,706,500; this device is also rudimentary in that the spoon badly fit to the eyelid, furthermore the coplanar arrangement of the arms does not permit the desired raising for a surgical operation. Still another example of known device is described in U.S. Pat. No. 2,702,540; the spoons of this device better fit to the eyelid, but the device is still very rudimentary and in particular it does not permit the desired raising. All these devices are inscribed in the strategy of the operative safety, the analysis of which is the condition for the actual success of the surgery. This analysis comprises an exhaustive study of all the instruments which are to be used by the surgeon, particularly for the retraction of the eyelids, which is a preliminary step in connection with any eye operation. All the basic elements of this surgery are described in the book entitled EYE SURGERY, Georg Eisner, Springer Verlag, 1980. Pages 73 to 78 in particular give information concerning the particular mechanical properties which have to be possessed by the devices which are related to the said description. It is particularly mentioned therein that the eyeball should no longer be in contact with the rims of the eyelids, not the retractor proper. It has now been found that the existing devices do in fact have numerous disadvantages.

Therefore it is also the object of the present invention, such as claimed herein, to obviate these disadvantages by providing a retractor device for human or animal tissue, and more particularly for retracting upper and lower eyelids to expose the underlying eyeball for surgery, comprising:
- a pair of retracting arms each having corresponding first and second ends;
- a pair of corresponding spoons, each having a first curvature adapted to the shape of an eyeball and a second curvature adapted to the shape of an eyelid, articulatingly mounted to the first ends of said retracting arms to pivot about axes that are in substantially perpendicular relationship with said retracting arms; and
- retracting means disposed at the second ends of said retracting arms joining said second ends in a cooperating relationship and biasing the first ends of said retracting arms into retracted positions.

Figure 1A:
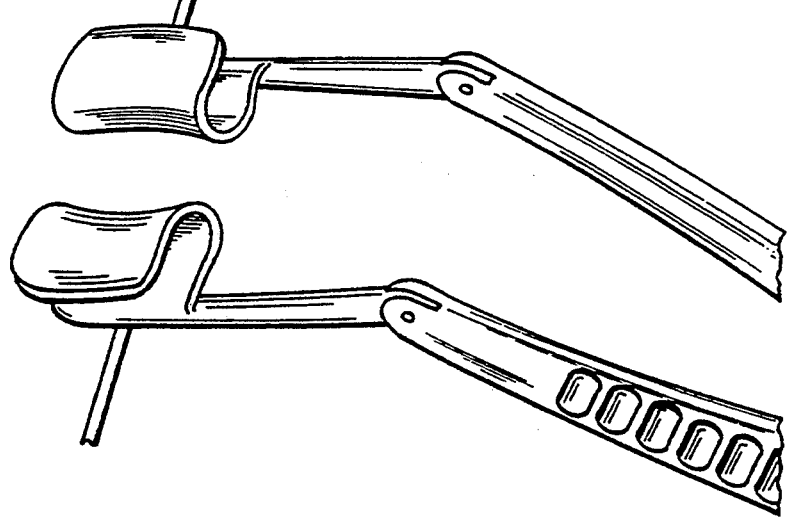
Figure 2:
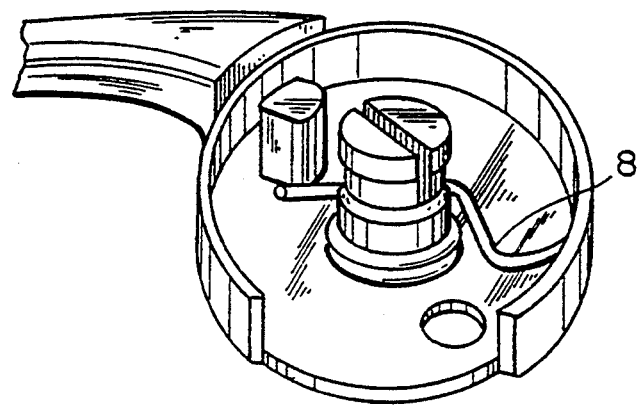
Figure 3:
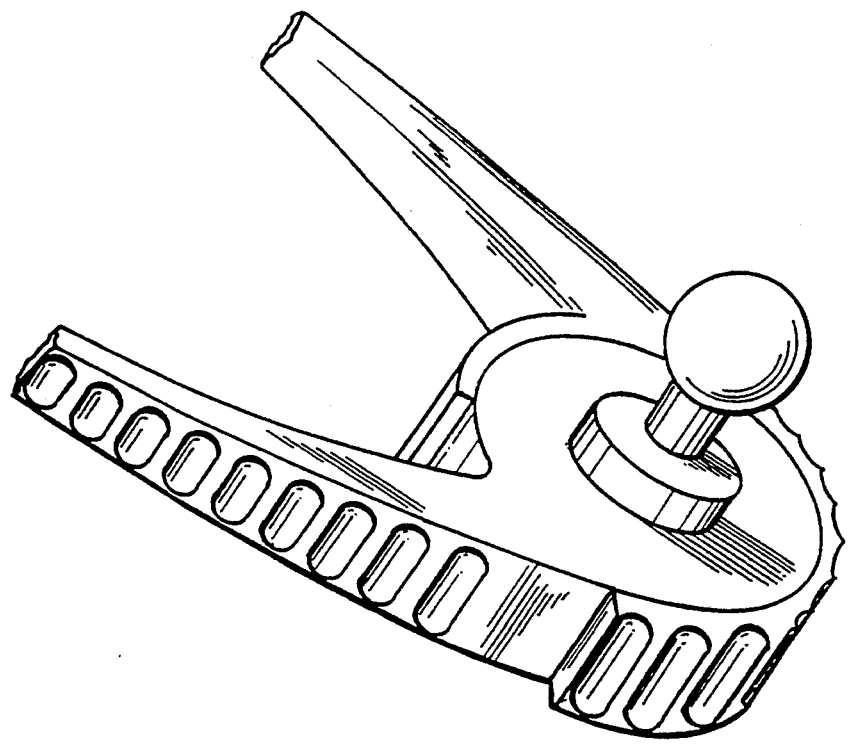
Figure 3A:
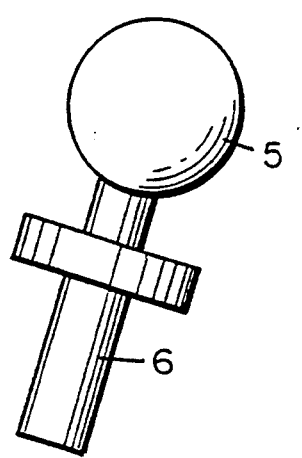
Figure 3B:
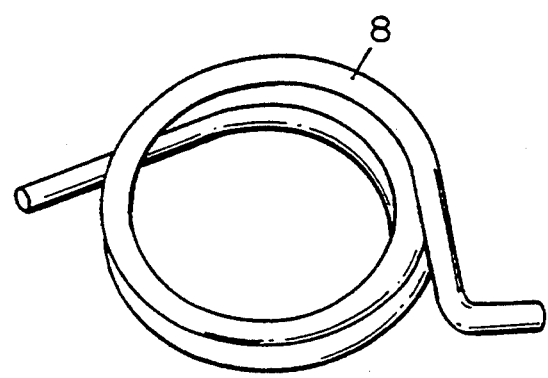
Figure 4:
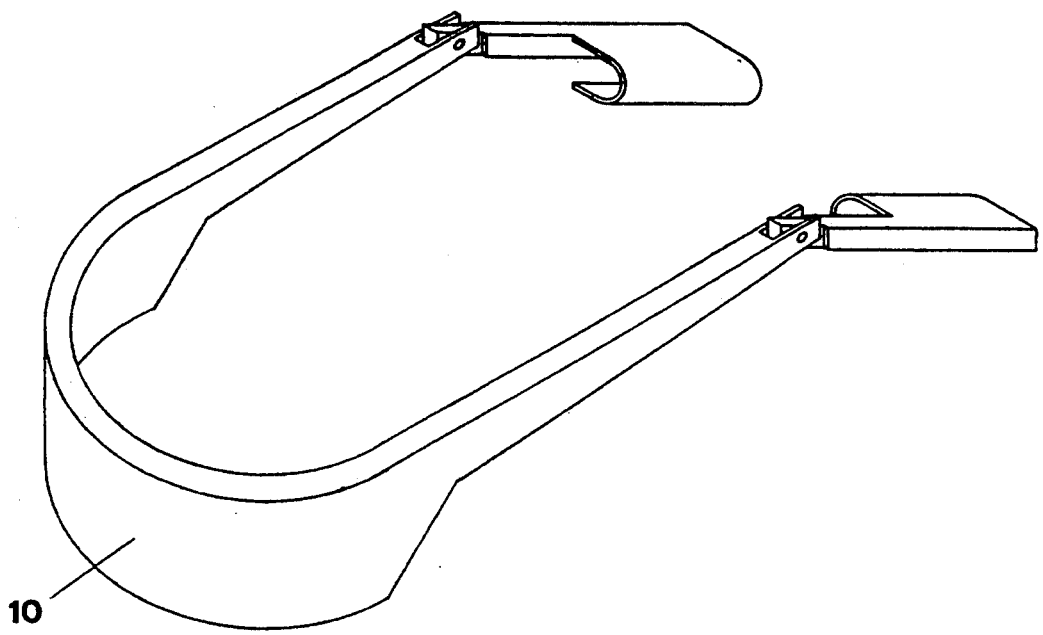

One embodiment of the retractor device according to the invention is now to be described, by way of example, by reference to the accompanying drawings, wherein:

FIG. 1 is a view of a first embodiment of the retractor device, seen in elevation and showing its application during an eye operation, FIG. 1a is an enlarged partial view of the retractor of FIG. 1, FIG. 2 is a detail view of the spoons and the casing of the retractor of FIG. 1, FIG. 3, 3a and 3b are detail views of the casing and its arbor, of the retracor of FIG. 1, and FIG. 4 is a schematic view seen in elevation of a second embodiment of the retractor device.

According to a first embodiment of the retractor device, the general arrangement, such as that shown in FIG. 1, is characterized in that the separate parts by which the desired object is achieved are: the spoons 2, the strips 7, the arms 1, the casing 3, the spindle 6, the ball-and-socket joint 5, the foot 4. All these elements are connected to one another in such manner that, once stuck on the temple, the device, by means of its arms, holds the lower and upper eyelids spaced and raised, from the time when their free edge is engaged in the concavity of the spoons 2. On the other hand, these latter are movable and articulated with the ends of the arms, in order to permit the desired raising, an action still maintained by the strips 7 bearing on the external face of the spoon 2 and held on the operative field by an adhesive. This mechanism assures the supplementary raising which could possibily be needed by the surgeon. The self-supporting character of this arrangement enables it to be used in the operating room and also in connection with certain functional explorations of the eye. In particular, this device permits the spacing apart and the raising of the eyelids, even on a seated patient.

The device as described comprises, at the end of each arm 1, a casing 3 in which is disposed a spring 8. This latter, brought under tension, tends automatically to retract the eyelids or the edges of any other operating field, without the cooperation of a second surgeon being necessary. The operative field is in this way freed from any element which reduces the freedom of the surgical movements and liable to make more difficult any access to the tissues.

Once the device as described is placed in position, it assures the raising of the eyelids relatively to the eyeball, as a consequence of the articulation which exists between the spoons 2 and the arms 1. What is thereby established is a palpebral circle, so-called as a safety circle, spacing the eyelids from the eyeball, so as to avoid these eyelids causing an excess of intraocular pressure. This is particularly useful in the case where there is local anasthesia of the eye, this process being increasingly used in the case of ambulatory operations, particularly of cataracts. The possibility of being able to use strips which extend to the interior of the spoons increases still more the spacing of the eyelids. The use of the adhesive strips or of clips permits the effect obtained to be maintained, while still assuring the immobility of the device, the foot of which is stuck by double face self-adhesive on the temporal side of the orbit, this assuring the immobility thereof.

Summarising, this device has three characteristics; it is self-supporting, self-retracting, self-elevating.

The spoons 2 are adapted to the shape of the eyeball and the eyelids, i.e. they have the curvatures required in the frontal and horizontal anatomic plane. Of variable dimensions, they are adapted to all the eyeball sizes, from the newly born to the adult. Contrary to other devices, they have a solid surface, in order to trap the eyelashes which would be able to come into contact with the instruments or the suture wires and cause infections. On the other hand, the pressure on the eyelids is more uniformly distributed, thus avoiding certain complications described with other devices, namely the post-operation paralyses of the upper eyelid. They have a gap in which fine strips are able to be slid, this contributing to the immobility of the said device. They are hinged with the arms, in order to permit a regulation of the function of raising.

The strips 7 make possible a regulation and maintenance of the desired raising, while at the same time forming fixation points for the operative field, thus permitting the stability of the assembly.

The arms 1 permit the transmission to the spoons 2 of the force liberated by the spring 8 under tension included in the casing 3. The arms 1 and the spoons 2 are hinged in a same plane.

The spring 8 makes possible to assure the auto-retraction function. By way of example, the scientific article described in OPHTALMIC SURGERY, Vol. 14, pages 575–578, 1983, gives values which permit of determining the force of the spring 8.

The spindle 6 and the ball-and-socket joint 5 permit of transmitting all the positions required in order to be adapted to the particular anatomic conditions of each patient.

The casing 3 may be separated from the spindle 6, in order to permit the surgeon to expose another part of the eyeball.

The lower face of the foot 4 is covered with a double face adhesive, permitting the adhesion of the external orbital wall, corresponding to the temple of the patient. The contact surface has been chosen so as to assure a maximum degree of immobility.

This device may be manufactured from all materials which have biocompatible properies.

Summarising, this retractor device offers the following advantages, as compared with the known devices:

1. Immobility. This is assured by three fixed points integral with the operative field and maintaining the palpebral circle spaced from the eyeball.
2. Adaptability. The device is adaptable to the anatomic angles by a first adjustment of the axis of the leg held in a foot and then by a fine adjustment, due to the pivoting of the spoons.
3. This device is profiled and designed in such manner that there is no risk of any screw or rod retaining and holding captive the surgical wires when they are placed in position.
4. The retraction of the eyelids is effected by solid surface spoons, having a slit situated on their front face, through which are passed two safety strips.
5. The symmetry of the device itself permits it to be positioned equally either on the right eye or on the left eye.
6. The device is so conceived that it can be injection moulded from medical plastic material, of which the advantage is, inter alia, its lightness. Moreover, it may be produced by moulding and injection in series, this reducing the cost of the device and permitting the single use thereof.
7. It is non-magnetisable.
8. It is radio-transparent.

A second embodiment of the retractor device is represented in FIG. 4. This arrangement is simplified in that it has no foot and does not comprise a spring nor a casing, but the arms are connected to each other by a bended portion 10, said bended portion and the arms forming a single-piece element. The auto-retraction function (made possible in the first embodiment by the spring) is here ensured on the one part by the elastic conformation of said bended portion of a single-piece element. The raising of the eyelids is simply obtained by pivoting the spoons with the fingers, the spoons remaining in position by the only friction of the articulation between the spoon and its respective arm.

Of course the above described second embodiment may also be provided, if so desired, with two strips and/or with an articulating foot of the type of the strips 7 and the foot 4 shown on FIG. 1.

I claim:

1. A retractor device for human or animal tissues, and more particularly for retracting upper and lower eyelids to expose the underlying eyeball for surgery, comprising:
    a pair of retracting arms formed from an elastic, single-piece element that has been configured into a U-shape, said pair of retracting arms each having corresponding end portions;
    a pair of corresponding spoons, each having a first curvature adapted to the shape of an eyeball and a second curvature adapted to the shape of an eyelid, articulatingly mounted to the end portions of said pair of retracting arms to pivot about axes that are in substantially perpendicular relationship with the end portions of said retracting arms whereby said second curvatures of said corresponding spoons raise the eyelids away from the eyeballs as the end portions of said pair of retracting arms are being biased into retracted positions under the influence of the elastic, single-piece element.

2. The retractor device of claim 1 wherein each of the spoons further comprises an elongated shaft, the articulatingly mounting of the spoon to the first end of said corresponding retracting arm being provided at the end of said shaft.

3. A retractor device for human or animal tissues, and more particularly for retracting upper and lower eyelids to expose the underlying eyeball for surgery, comprising:
    a pair of retracting arms formed from an elastic, single-piece element that has been configured into a U-shape, said pair of retracting arms each having corresponding end portions;
    a pair of corresponding spoons, each having a solid-surface first curvature adapted to the shape of an eyeball and a solid-surface second curvature adapted to the shape of an eyelid, articulatingly mounted to the first ends of said pair of retracting arms to pivot about axes that are in substantially perpendicular relationship with the end portions of said retracting arms whereby said second curvatures of said corresponding spoons raise the eyelids away from the eyeballs as the end portions of said pair of retracting arms are being biased into retracted positions under the influence of said elastic, single-piece element.

4. The retractor device of claim 3 wherein each of the spoons further comprises an elongated shaft, the articulatingly mounting of the spoon to the first end of said corresponding retracting arm being provided at the end of said shaft.

* * * * *